United States Patent
Masumura

(10) Patent No.: US 12,411,083 B2
(45) Date of Patent: Sep. 9, 2025

(54) MEASURING APPARATUS, MEASURING METHOD, AND STORAGE MEDIUM

(71) Applicant: CANON KABUSHIKI KAISHA, Tokyo (JP)

(72) Inventor: Takahiro Masumura, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 285 days.

(21) Appl. No.: 18/295,891

(22) Filed: Apr. 5, 2023

(65) Prior Publication Data

US 2023/0236126 A1 Jul. 27, 2023

Related U.S. Application Data

(63) Continuation of application No. PCT/JP2021/027930, filed on Jul. 28, 2021.

(30) Foreign Application Priority Data

Oct. 14, 2020 (JP) .................................. 2020-173529

(51) Int. Cl.
*G01N 21/49* (2006.01)

(52) U.S. Cl.
CPC .................................... *G01N 21/49* (2013.01)

(58) Field of Classification Search
CPC ... A61B 5/14552; G01N 21/49; G01N 21/645
See application file for complete search history.

(56) References Cited

U.S. PATENT DOCUMENTS 5,902,235 A * 5/1999 Lewis ................ A61B 5/14553
600/323
6,353,226 B1 * 3/2002 Khalil .................... G01N 21/49
600/323

(Continued)

FOREIGN PATENT DOCUMENTS

JP   2014500751 A   1/2014
JP   2016217860 A   12/2016

(Continued)

OTHER PUBLICATIONS

International Search Report issued in Intl. Appln. No. PCT/JP2021/027930 mailed Oct. 19, 2021. English translation provided.

(Continued)

*Primary Examiner* — Hina F Ayub
(74) *Attorney, Agent, or Firm* — ROSSI, KIMMS & McDOWELL LLP

(57) ABSTRACT

A measuring apparatus is configured to acquire information on a target. The measuring apparatus includes an irradiating unit configured to irradiate a specific area of the target with irradiation light, a detecting unit configured to receive exit light from the target which is caused by irradiating the specific area with the irradiation light, and a processing unit configured to process a signal output from the detecting unit. The processing unit causes the irradiating unit to shape a wavefront of the irradiation light by feeding back a first signal output from the detecting unit that has received the exit light. The processing unit acquires information about the specific area using a second signal output from the detecting unit that has received exit light from the target which is by irradiating the specific area with irradiation light having a shaped wavefront.

11 Claims, 4 Drawing Sheets

(56) References Cited

U.S. PATENT DOCUMENTS

| | | |
|---|---|---|
| 2012/0182591 A1 | 7/2012 | Masumura |
| 2015/0018646 A1* | 1/2015 | Gulati .................. A61B 5/1079 600/322 |
| 2015/0313516 A1 | 11/2015 | Shimizu et al. |
| 2016/0338592 A1 | 11/2016 | Masumura |

FOREIGN PATENT DOCUMENTS

| | | |
|---|---|---|
| JP | 6241853 B2 | 12/2017 |
| JP | 2018100923 A | 6/2018 |

OTHER PUBLICATIONS

Written Opinion issued in Intl. Appln. No. PCT/JP2021/027930 mailed Oct. 19, 2021.

Popoff. "Measuring the Transmission Matrix in Optics: An Approach to the Study and Control of Light Propagation in Disordered Media" Physical Review Letters. Mar. 12, 2010: 100601-1-100601-4. vol. 104. Cited in NPL1.

Vellekoop. "Focusing coherent light through opaque strongly scattering media" Optics Letters. Aug. 15, 2007: 2309-2311. vol. 32, No. 16. Cited in NPL1.

English translation of Written Opinion issued in Intl. Appln. No. PCT/JP2021/027930 mailed Oct. 19, 2021, previously cited on Apr. 5, 2023.

International Preliminary Report on Patentability issued in Intl. Appln. No. PCT/JP2021/027930 mailed Apr. 27, 2023. English translation provided.

\* cited by examiner

MEASURING APPARATUS, MEASURING METHOD, AND STORAGE MEDIUM

CROSS-REFERENCE TO RELATED APPLICATIONS

This application is a Continuation of International Patent Application No. PCT/JP2021/027930, filed on Jul. 28, 2021, which claims the benefit of Japanese Patent Application No. 2020-173529, filed on Oct. 14, 2020, both of which are hereby incorporated by reference herein in their entirety.

BACKGROUND

Technical Field

One of the aspects of the disclosure relates to a measuring apparatus, a measuring method, and a storage medium for acquiring information on an object to be measured (referred to as a target hereinafter) using light.

Description of Related Art

Japanese Domestic PCT Publication No. 2014-500751 discloses a method and apparatus for extracting a parameter in blood, such as blood hemoglobin concentration and oxygen saturation, by measuring dynamic changes in blood in a living body using dynamic light scattering (DLS). Japanese Patent No. 6241853 discloses a measuring apparatus for noninvasively measuring a scattering coefficient in an area including a vascular region and calculates the serum lipid concentration from the scattering coefficient.

The methods disclosed in Japanese Domestic Publication No. 2014-500751 and Japanese Patent No. 6241853 can noninvasively and easily measure a target. However, these methods do not shape a wavefront of light during measurement, and thus have difficulty in accurately acquiring information about the target, such as minute changes in physiological parameters in a living body, due to the influence of light scattering.

SUMMARY

One of the aspects of the present disclosure provides a measuring apparatus, a measuring method, and a storage medium, each of which can acquire information on a target with high accuracy using light.

A measuring apparatus according to one aspect of the disclosure is configured to acquire information on a target. The measuring apparatus includes an irradiating unit configured to irradiate a specific area of the target with irradiation light, a detecting unit configured to receive exit light from the target which is caused by irradiating the specific area with the irradiation light, and a processing unit configured to process a signal output from the detecting unit. The processing unit causes the irradiating unit to shape a wavefront of the irradiation light by feeding back a first signal output from the detecting unit that has received the exit light. The processing unit acquires information about the specific area using a second signal output from the detecting unit that has received exit light from the target which is by irradiating the specific area with irradiation light having a shaped wavefront. A measuring method corresponding to the above measuring apparatus and a non-transitory computer-readable storage medium storing a program that causes a computer to execute the measuring method also constitute another aspect of the disclosure.

Further features of the disclosure will become apparent from the following description of embodiments with reference to the attached drawings.

DESCRIPTION OF THE EMBODIMENTS

Referring now to the accompanying drawings, a detailed description will be given of embodiments according to the disclosure.

First Embodiment

Figure 1:
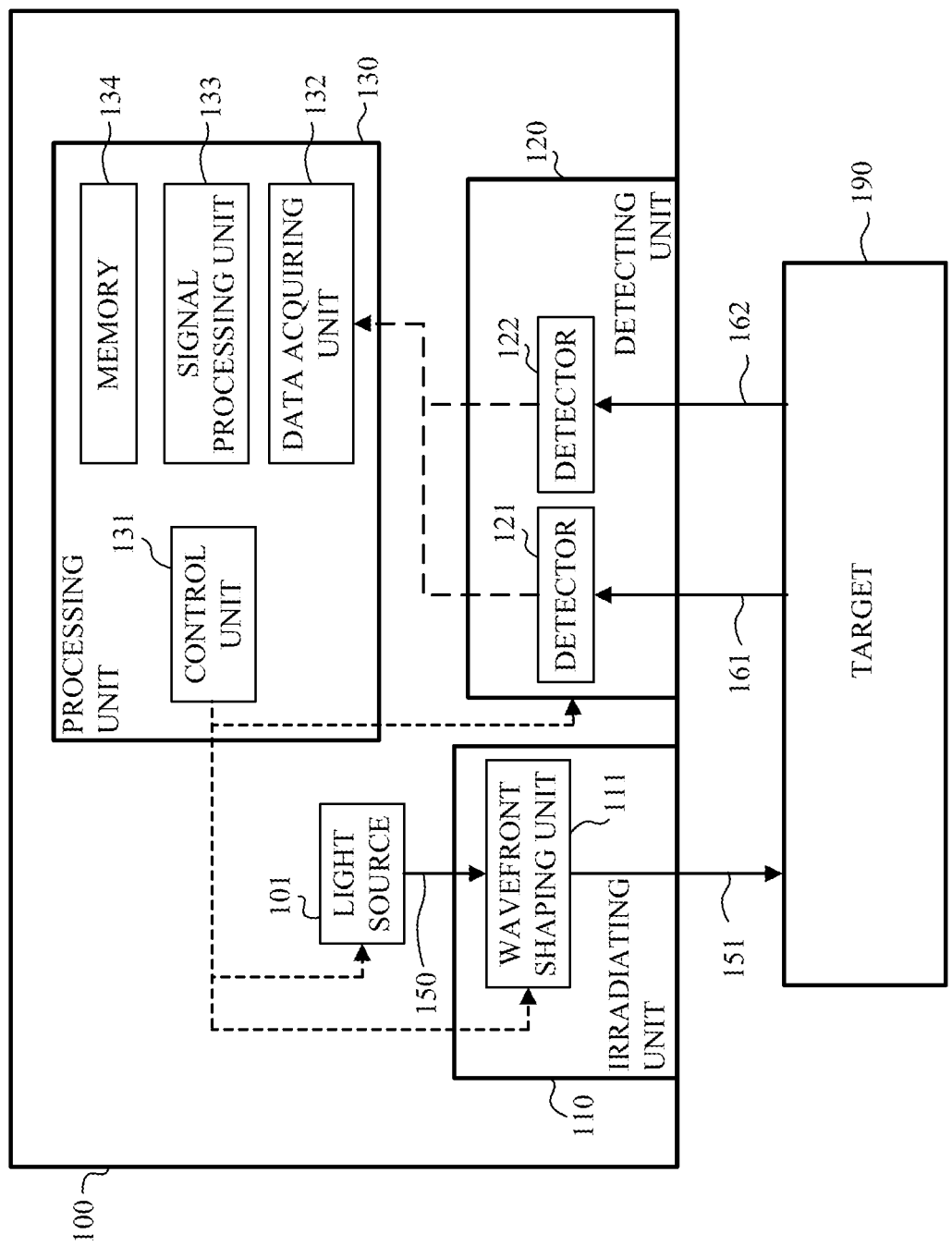
FIG. 1 is a block diagram of a measuring apparatus according to a first embodiment.

Referring now to FIG. 1, a description will be given of a measuring apparatus according to a first embodiment of the disclosure. FIG. 1 is a block diagram of a measuring apparatus (target measuring apparatus) 100 according to this embodiment. The measuring apparatus 100 according to this embodiment can acquire information on a target and includes a light source 101, an irradiating unit 110, a detecting unit 120, and a processing unit 130. The irradiating unit 110 irradiates a specific area of a target 190 with light emitted from the light source 101 as irradiation light 151. The detecting unit 120 receives exit lights 161 and 162 from the target 190 which are caused by irradiating the specific area of the target 190 with the irradiation light 151. The processing unit 130 processes a signal output from the detecting unit 120 and includes a control unit 131, a data acquiring unit 132, a signal processing unit 133, and a memory 134.

The light source 101 includes, for example, a laser that emits light with a wavelength of 300 nm to 1200 nm, which is continuous light (CW light: continuous wave light) whose intensity is constant over time. For example, the wavelength can be selected according to the absorption spectrum of the item to be measured from water, fat, protein, oxygenated hemoglobin, reduced hemoglobin, etc., which are the main constituents of the target 190. Alternatively, in measuring a scattering coefficient, a wavelength other than the above absorption wavelength may be selected. Depending on the purpose, the wavelength may be selected outside the above range, and the laser may emit intensity-modulated light with an arbitrary frequency or pulsed light. The irradiation light may have a sufficiently long coherence length (such as several centimeters or longer). The intensity of the light irradiated to the target 190 is adjusted within the intensity that can be irradiated under the safe standard.

Light 150 emitted from the light source 101 is collimated and enters a wavefront shaping unit 111 in the irradiating unit 110. The wavefront shaping unit 111 includes a spatial light modulator (SLM). The SLM may be a phase modulation type or an amplitude modulation type. The wavefront shaping unit 111 may also be either a transmission type or reflection type SLM. More specifically, the SLM can use an LCOS (Liquid Crystal On Silicon), a DMD (Digital Mirror Device), a GLV (Grating Light Valve), or the like. The SLM may be able to modulate light as fast as possible (such as at several kHz or higher).

The wavefront shaping unit 111 performs wavefront shaping (WFS), which will be described below, and irradiates the target 190 with light having a shaped wavefront as irradiation light 151. The wavefront shaping unit 111 shapes the wavefront of the irradiation light 151 by performing phase modulation or amplitude modulation based on a base pattern. At this time, the irradiating unit 110 may include an optical system for irradiating collimated light or converged light of any beam size. Alternatively, the irradiating unit 110 may include an optical fiber, and irradiate the target 190 with the light shaped by the wavefront shaping unit 111 via the optical fiber.

The exit lights 161 and 162 that have propagated inside the target 190 and exited at different distances from an irradiating position on the surface of the target 190 are received by a detector (first detector) 121 and a detector (second detector) 122 in the detecting unit 120, respectively. The detecting unit 120 may include an optical system for condensing the exit lights 161 and 162 from the target 190 onto the detectors 121 and 122. Alternatively, the exit lights 161 and 162 may be guided to detectors 121 and 122, respectively, via optical fibers. The detectors 121 and 122 can use sensors such as photodetectors (PD), avalanche photodiodes (APD), and photomultiplier tubes (PMT). Alternatively, a two-dimensional array sensor such as a CMOS or a CCD can be used. The detectors 121 and 122 may respond at high speed (>1 MHz).

The light intensities received by the detectors 121 and 122 are converted into electrical signals, and passed to the data acquiring unit 132. The data acquiring unit 132 amplifies the signal with an amplifier circuit as necessary, performs analog-to-digital (A/D) conversion for the amplified signal, and generates a digital signal. The signal processing unit 133 performs various signal processing for the digital signal as necessary. The memory 134 properly stores measurement results, intermediate information during measurement, and the like. The memory 134 also stores a measurement flow, measurement conditions, parameters necessary for analysis, and the like. The signal processing unit 133 properly accesses the memory 134 according to the processing, refers to necessary information, and executes the processing.

The control unit 131 controls each module in the light source 101, the irradiating unit 110, the detecting unit 120, and the processing unit (data acquiring unit 132, signal processing unit 133, and memory 134) in the measuring apparatus 100 based on the measurement flow (measuring method), which will be described below.

Figure 2:
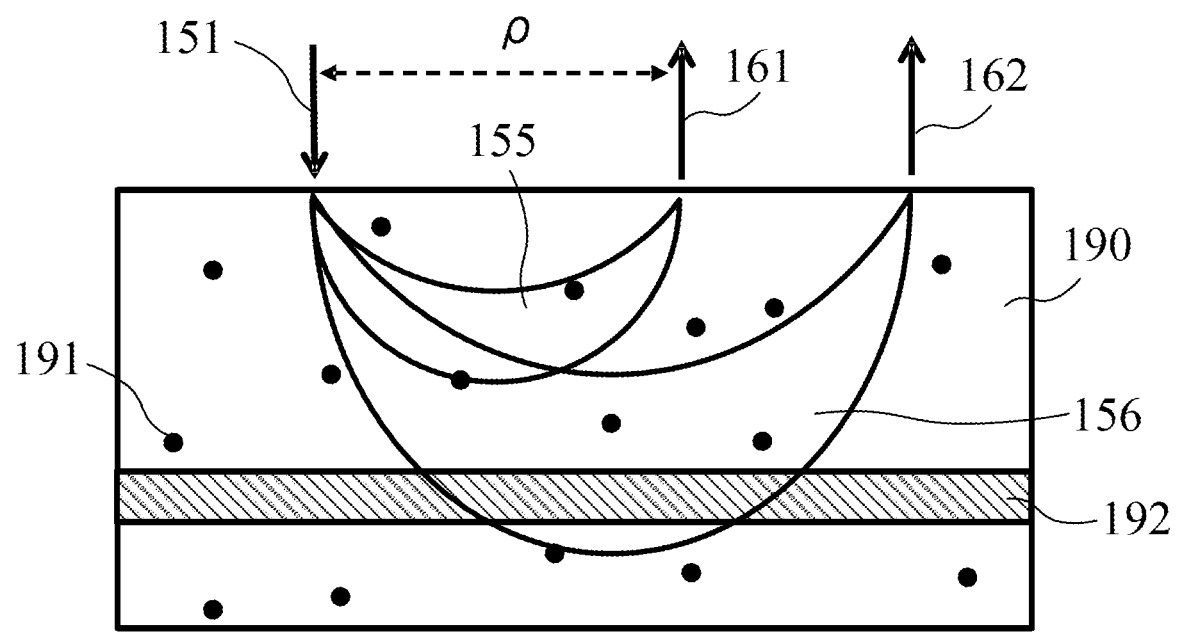
FIG. 2 is a schematic diagram of a light propagation path in the first embodiment.

Referring now to FIG. 2, a description will be given of propagation paths of the irradiation light 151 that is emitted from the irradiating unit 110, propagates inside the target 190, and exits. FIG. 2 schematically illustrates the propagation paths of the irradiation light 151 that is emitted from the irradiating unit 110, propagates inside the target 190, and exits. The irradiation light 151 is influenced by a scatterer 191 derived from cells and tissue structures inside the target 190 and propagates inside the target 190 while being repeatedly scattered. From the light irradiating position at which the irradiation light 151 enters the target 190, the path along which the exit light propagates inside the target 190 differs depending on a distance $\rho$ in the horizontal direction. For example, the spreading banana-shaped distribution illustrated in the propagation path 155 is shown at the exit position of the exit light 161. Similarly, the distribution like the propagation path 156 is shown at the exit position of the exit light 162.

In a case where the two propagation paths 155 and 156 are compared, the propagation path 156 penetrates and propagates to a deeper area in the target 190. That is, as the distance $\rho$ between the irradiating position and the detection position increases, the detected exit light is light that has propagated to a deeper position in the target 190 and reflects the optical characteristics of a deeper position inside the target 190. This propagation path can be estimated based on the absorption coefficient and scattering coefficient, which are the optical characteristics of the target 190, using the radiation transport equation or the diffusion equation as its diffusion approximation. That is, adjusting the distance $\rho$ can specify the light propagating area in the depth direction inside the target 190.

The detecting unit 120 can arbitrarily set the detection positions (distance $\rho$) at which the detectors 121 and 122 receive the lights so as to measure the exit lights from the arbitrary exit positions on the surface of the target 190. As illustrated in FIG. 2, the distance $\rho$ is set such that the detector 121 detects the exit light 161 that has propagated through a specific area (first area: area that contains no blood vessel (non-vascular area)) near the surface of the target 190. On the other hand, the distance $\rho$ is set such that the detector 122 detects the exit light 162 that has propagated through a vascular region 192 (second area: area that contains a blood vessel (vascular area)) which is a relatively deep specific area in the target 190.

Figure 3:
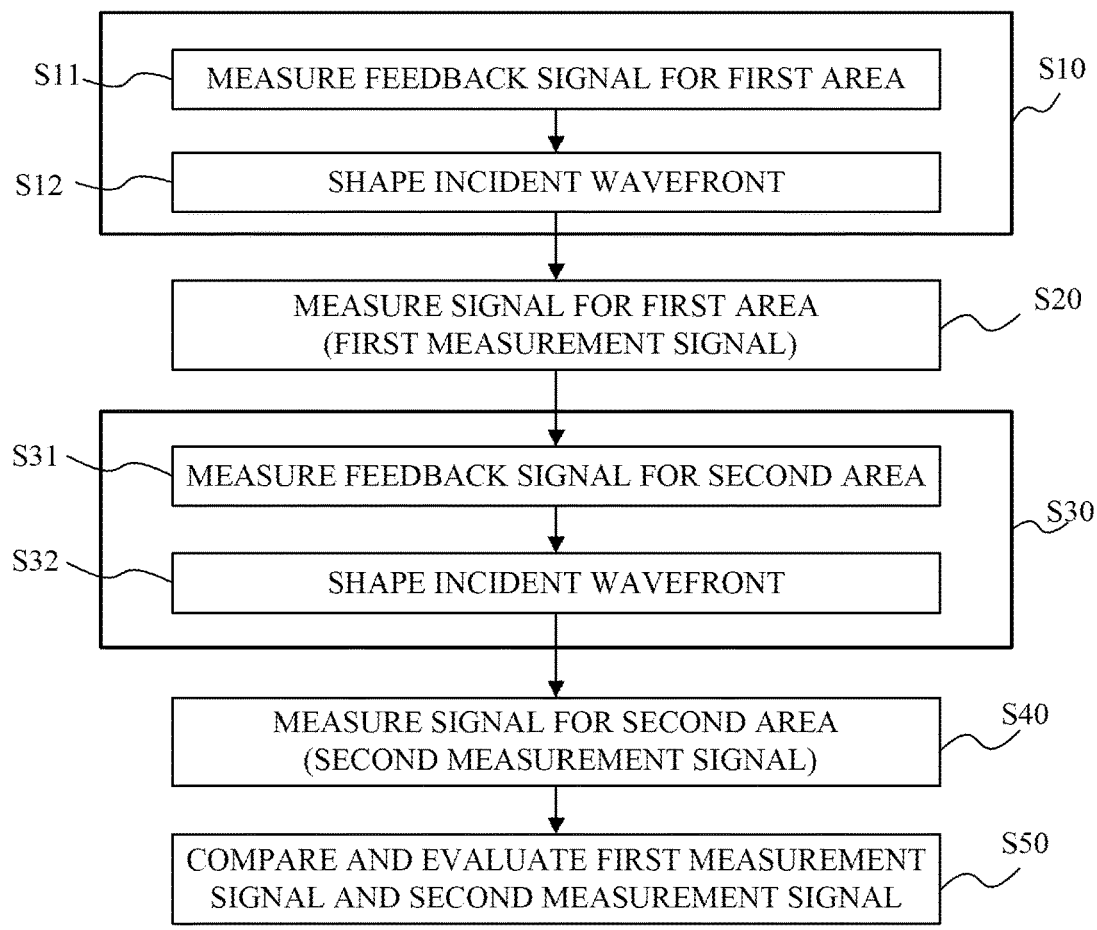
FIG. 3 is a flowchart of a measuring method according to the first and second embodiments.

Referring now to FIG. 3, a description will be given of the measuring method according to this embodiment. FIG. 3 is a flowchart of the measuring method according to this embodiment. Each step in FIG. 3 is mainly executed by the irradiating unit 110, the detecting unit 120, and the processing unit 130 in the measuring apparatus 100.

First, in step S10, the processing unit 130 measures the exit light 161 and performs WFS based on the signal intensity of the light that has propagated through the first area (non-vascular area). The WFS shapes (optimizes) the wavefront (phase distribution or amplitude distribution) of the irradiation light 151 incident on the target 190 so as to maximize or minimize the monitored feedback signal (first signal). More specifically, step S10 includes steps S11 and S12.

First, in step S11, the processing unit 130 measures the optical intensity measured by the detector 121 as a feedback signal. This light intensity is the average value of the light intensities received by the detector 121 for a certain period. Next, in step S12, the processing unit 130 performs wavefront shaping for the irradiation light 151 using the wavefront shaping unit 111. That is, the processing unit 130 feeds back the first signal (first feedback signal) from the detecting unit 120 that has received the exit light 161 that has propagated through a non-vascular area (first area) and exited from the target 190, and causes the irradiating unit 110 to shape the wavefront of the irradiation light 151. The wavefront shaping can be performed based on a modulation pattern (base pattern), such as a Hadamard basis, displayed on the SLM (wavefront shaping unit 111).

Figure 4:
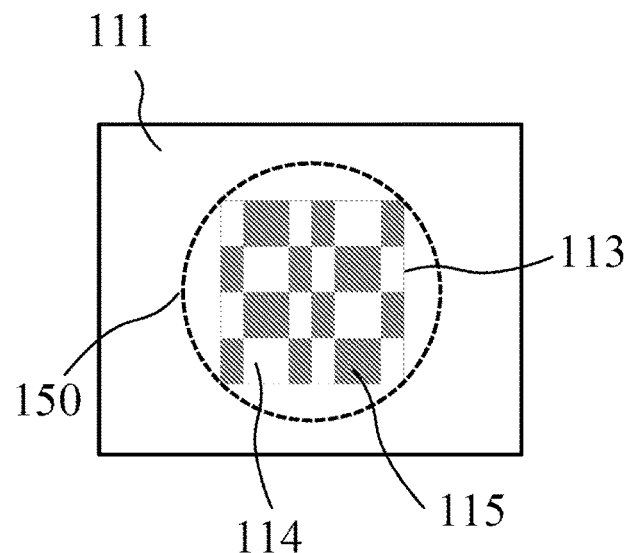
FIG. 4 is a schematic diagram of a wavefront shaping unit and a modulation pattern in the first embodiment.

Referring now to FIG. 4, a description will be given of the modulation pattern. FIG. 4 schematically illustrates the SLM (wavefront shaping unit 111) and a modulation pattern. A modulated pattern 113 is displayed on the SLM, and the modulated pattern 113 is irradiated with the light 150 emitted from the light source 101. A white portion 114 in the modulation pattern 113 represents a non-modulated area where the phase is not modulated, and a gray portion 115 represents a modulated area where the phase is modulated. In the modulated area, the phase is modulated by an arbitrary number of steps with respect to the non-modulated area, and the target 190 is irradiated with the irradiation light 151 modulated by the phase. Again, in step S11, the control unit 131 measures the feedback signal. Steps S11 and S12 are repeated the number of steps to search for the phase that maximizes the feedback signal, and SLM is set (N=1). Steps S11 and S12 are executed for an arbitrary number N of modulation patterns. After step S10 (iterative processing of steps S11 and S12) is executed the arbitrary number N of modulation patterns, the processing unit 130 ends the WFS for the first area. While FIG. 4 uses a two-dimensional SLM and illustrates an example of the two-dimensional modulation pattern 113, a one-dimensional SLM may be used and a one-dimensional modulation pattern may be used.

After step S10 ends, the flow proceeds to step S20. In step S20, the processing unit 130 causes the irradiating unit 110 to irradiate the target 190 with the irradiation light 151 having the wavefront shaped in step S10, performs the DLS, and acquires a first measurement signal (second signal). More specifically, the processing unit 130 uses the detector 121, causes the irradiating unit 110 to continuously irradiate the target 190 with the irradiation light (first irradiation light) 151 having the wavefront shaped (optimized) in step S10, and measures changes in light intensity of the exit light 161 over time. That is, the processing unit 130 causes the irradiating unit 110 to irradiate the target 190 with the first irradiation light having the shaped wavefront and measures the second signal (calculates correlation function g(τ)). The correlation function g(τ) is expressed as in Equation (1) below:

$$g(\tau) = \frac{<I(t)I(t+\tau)>}{<I(t)>^2} \quad (1)$$

where I(t) is the light intensity at time t, τ is the delay time, and < > is averaging.

Figure 5:
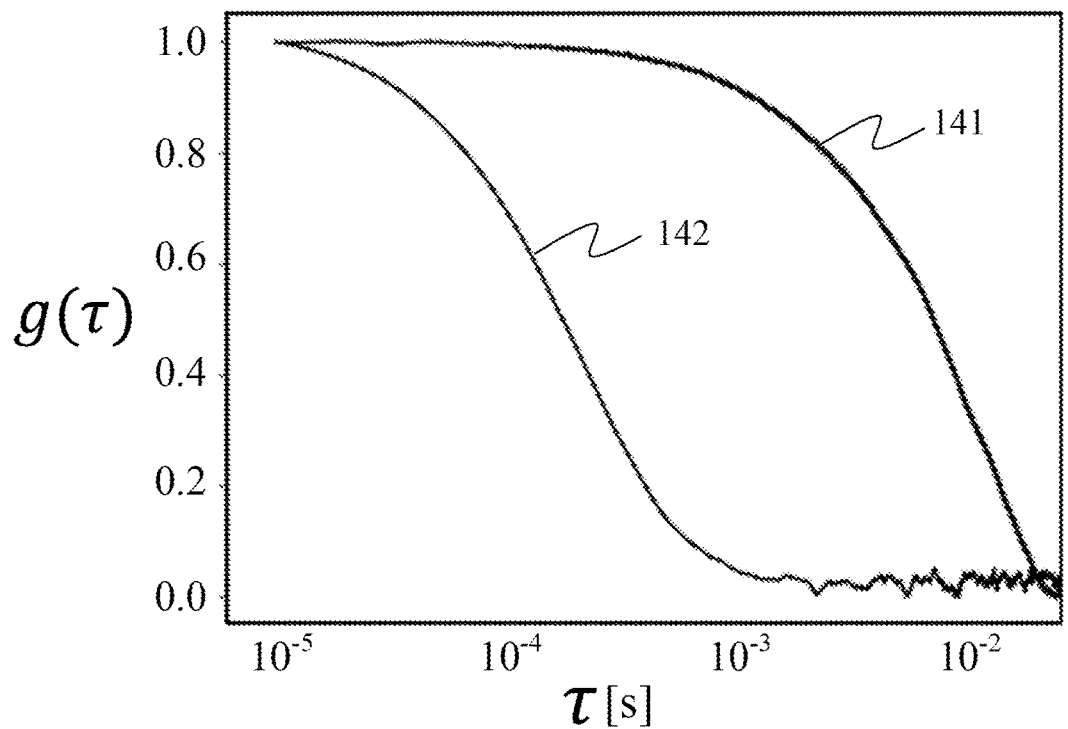
FIG. 5 illustrates an example of a measurement signal in the first embodiment.

A hardware correlator may be used to calculate the correlation function g(τ). That is, the detecting unit 120 has a correlator, outputs the correlation function g(τ) from the output signal from the detector, and passes it to the data acquiring unit 132. Alternatively, the correlation function g(τ) may be calculated using software. For example, the light intensity I(t) received by detecting unit 120 may be received by data acquiring unit 132 and stored in the memory 134. Next, the signal processing unit 133 may read the light intensity I(t) from the memory 134 and calculate the correlation function g(τ) by digital signal processing. FIG. 5 illustrates an example of the measured correlation function g(τ), that is, the measurement signal. In FIG. 5, a horizontal axis represents the delay time τ[s] and a vertical axis represents the correlation function g(τ). In this embodiment, a correlation function 141 measured in step S20 is the first measurement signal (the second signal relating to the first area).

Next, in steps S30 and S40, the processing unit 130 performs the same processing as steps S10 and S20 for the detected position of the exit light 162, respectively. More specifically, first, in step S30, the processing unit 130 sets the light intensity of the exit light 162 received by the detector 122 to a feedback signal and performs the WFS so as to maximize the feedback signal. As described above, the processing unit 130 measures the feedback signal using the detecting unit 120 in step S31, and shapes the wavefront of the irradiation light 151 using the wavefront shaping unit 111 in step S32. That is, the processing unit 130 feeds back the first signal (second feedback signal) from the detecting unit 120 that has received the exit light 162 that has propagated through a vascular area (second area) and exited from the target 190, and causes the irradiating unit 110 to shape the wavefront of the irradiation light 151. The control unit 131 repeats the iterative processing of steps S31 and S32 N times, which is the number of patterns, and optimizes the wavefront of the irradiation light 151 so as to maximize the intensity of the exit light 162 that has propagated through the second area (vascular area).

Here, a constraint condition may be imposed so that the exit light 162 selectively propagates through the second area. For example, in optimizing the wavefront of the irradiation light 151, the WFS of step S32 may have a constraint condition that minimize the light intensity of the exit light 161 output from the detector 121 and maximizes the light intensity of the exit light 162 output from the detector 122. The wavefront of the irradiation light 151 may be optimized under the constraint condition such that the signal intensity of the light that propagates through the vascular region 192 in the deep part of the target 190 and exits is maximized while the light that propagates through the surface layer of the target 190 is suppressed. Due to this WFS, the S/N ratio of the feedback signal to be measured can be improved while the propagation area is specified.

After step S30 ends, the flow proceeds to step S40. In step S40, the processing unit 130 causes the irradiating unit 110 to irradiate the target 190 with the irradiation light 151 having the wavefront shaped in step S30, performs the DLS, and acquires the correlation function g(τ) similarly to step S20. That is, the processing unit 130 causes the irradiating unit 110 to irradiate the target 190 with irradiation light (second irradiation light) 151 having the shaped wavefront and measures the second signal. For example, in step S40, a correlation function 142 illustrated in FIG. 5 is measured. This second signal is a second measurement signal (second signal relating to the second area). The measurement is thus completed, and all the measured data are stored in the memory 134 by the data acquiring unit 132.

Next, in step S50, the processing unit 130 compares and evaluates the first measurement signal measured in step S20 and the second measurement signal measured in step S40. That is, the processing unit 130 acquires information on the target 190 by comparing a second signal based on the first irradiation light and a second signal based on the second irradiation light. The first measurement signal is the light that has propagated through the surface layer of the target 190 as described above, and since there are almost no elements that dynamically change scattering, the change in scattering over time is small. On the other hand, the second measurement signal is influenced by the vascular region 192 that dynamically changes scattering, and thus the change in scattering over time is large.

Therefore, as illustrated in FIG. 5, it takes a long time τ for the correlation function of the first measurement signal to decay, whereas it takes a relatively short time for the correlation function of the second measurement signal to decay. Therefore, the first measurement signal whose results are relatively stable is set to reference data, and how much the second measurement signal is changed relative to the reference data can be relatively measured. For example, as a method of comparing and evaluating these two signals, each correlation function g(τ) may be fitted with an exponential function exp(−Γτ) to calculate the decay coefficient Γ and the fitted correlation functions may be compared. The decay coefficients of the first measurement signal and the second measurement signal are set to $\Gamma_1$ and $\Gamma_2$, respectively, and changes of a ratio $\gamma=\Gamma_2/\Gamma_2$ or a difference $\gamma=\Gamma_2-\Gamma_1$ over time may be monitored. Although FIG. 5 illustrates the normalized correlation function, normalization is not necessary, and the measured correlation function can be evaluated through various analyzes other than the decay coefficient. Delay times until each correlation function decays to a certain value may be compared without fitting.

The measurement flow according to this embodiment has thus been described. Pre-measurement for determining measurement conditions and measurement parameters may be performed before step S10. The detection positions ρ for the exit lights 161 and 162, WFS-related parameters, DLS measurement conditions, and the like may be determined based on the result of the pre-measurement.

Here, this embodiment uses the DLS as a method for acquiring the information on the target 190 (biological physiological parameters). In the DLS, as described above, temporal variations in scattered light are reflected in the correlation function. For example, an element that provides a dynamic variation to the scattered light such as the bloodstream, and an element that provides a light intensity variation as an average bias component can be distinguished by delay time τ or frequency analysis. The latter is, for example, a system error on the light source or detection side, or an error component such as light absorption that does not locally change with time in the target 190. Therefore, obtaining a measurement signal using the DLS can reduce the influence of error factors and acquire biological information more robustly than simply measuring light intensity. The correlation function varies depending on physiological parameters of a living body, such as a scattering coefficient in blood and the blood flow (bloodstream) rate.

Therefore, setting the vascular region 192 as a target to be measured and monitoring changes over time of the decay coefficient $\Gamma_2$ of the second measurement signal can monitor changes in the blood scattering characteristic. For example, the more significant the blood scattering is, the larger the decay coefficient $\Gamma_2$ is. Thus, the measurement flow illustrated in FIG. 3 using the measuring apparatus 100 according to this embodiment can monitor changes in the optical characteristic such as blood scattering. In addition, this method can measure a blood hemoglobin amount and other physiological parameters relating to blood such as oxygen saturation based on the DLS measurement result, by changing the wavelength of the light source 101 and.

This embodiment can measure scattered light that reflects the optical characteristic of a specific area (first area or second area) inside the target 190 with an improved S/N ratio by applying the WFS and maximizing the feedback signal. Moreover, in measuring the physiological parameters of the target 190, this embodiment measures another signal, which is a DLS-based correlation function, instead of directly using the feedback signal. The feedback signal varies depending on the WFS measurement condition, such as the number of patterns N. In other words, since the feedback signal is a signal controllable on the device side, the measurement result cannot be directly used as a signal for measuring biological information. Therefore, this embodiment acquires another measurement signal that can utilize the effect of improving the feedback signal by the WFS.

In a case where the effect of improving the S/N ratio by the WFS is lost in the measurements of steps S20 and S40, the WFS in steps S10 and S30 may be re-executed, and then the measurements in steps S20 and S40 may be re-executed. For example, the feedback signal may be monitored in step S20 or step S40 and the feedback signal may be compared with a preset threshold to determine whether to re-execute the WFS. The feedback signal can use another signal, as will be described in another embodiment below.

In this embodiment, the processing unit 130 may measure the measurement signal (second signal) based on a parameter relating to the decay or delay time of the correlation function. The first detector (detector 121) may receive the exit light that has propagated through the first area (non-vascular area) as the specific area and exited from the target, and the second detector (detector 122) may receive the exit light that has propagated through the second area (vascular area) as the specific area and exited from the target.

In this embodiment, in a case where the signal intensity of the exit light 161 has a sufficient S/N ratio in step S11, step S10 may be omitted. In this case, the measurement can be started with step S20. Although the two detectors 121 and 122 are provided in this embodiment, the number of detectors is not limited to two. In a case where a single detector is provided, steps S10 and S20 may be omitted, and only the second measurement signal may be measured by performing steps S30 and subsequent steps. In this case, step S50 does not perform the comparison or evaluation, and can output the result of the second measurement signal. Three or more detectors may be provided so that a measurement area of the target 190 is limited for each detector, the WFS may be executed for each detector to acquire the measurement signal, and the results may be evaluated.

Second Embodiment

A description will now be given of a second embodiment according to the disclosure. The measuring apparatus according to this embodiment has the same basic configuration as that of FIG. 1, but the detecting unit 120 includes a single detector 121. The measuring method according to this embodiment follows the flowchart illustrated in FIG. 3. This embodiment uses the single detector 121 to perform two measurements for the first non-vascular area and the second vascular area described in the first embodiment, and compare and evaluate the two measurement results.

Figure 6:
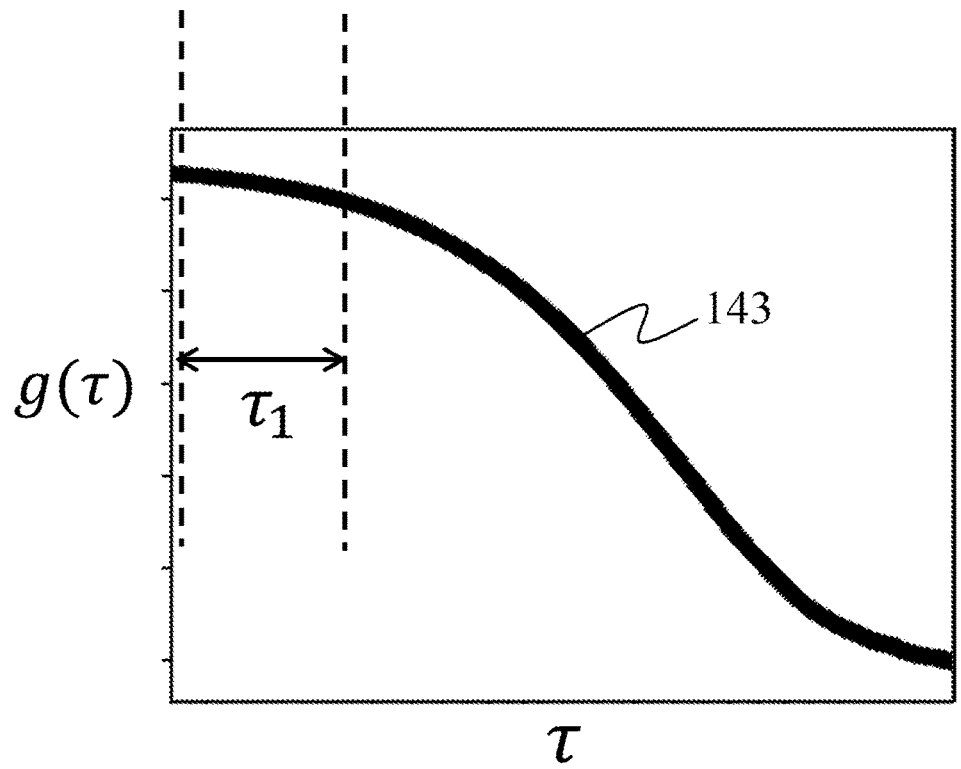
FIG. 6 explains a feedback signal in the second embodiment.

First, in step S10 of FIG. 3, the control unit 131 executes the WFS so as to measure the first area near the surface layer of the target 190. A signal based on the correlation function g(τ) obtained by executing the DLS is used as the feedback signal for the WFS. FIG. 6 explains a correlation function 143 obtained by measuring the time variation of the intensity of the exit light 161 with the detector 121. In FIG. 6, a horizontal axis represents the delay time τ, and a vertical axis represents the correlation function g(τ). Here, a part of the correlation function 143 may be used as the feedback signal. For example, the part of the correlation function 143 may be a value of the correlation function (feedback signal $g(\tau_1)$) when the delay time $T_1$ has passed.

As illustrated in the flowchart of FIG. 3, this feedback signal $g(\tau_1)$ is monitored in step S11, the phase of the modulation pattern is changed in step S12, and the feedback signal is again monitored in step S11. For the fast iterative processing of step S10, the acquisition time of the feedback signal may be shortened. Therefore, the delay time $T_1$ is made as short as possible. On the other hand, for the second area in which a dynamic change in the target 190 is expected, the setting may be made within a detectable range of the change in the feedback signal value $g(\tau_1)$.

In step S12, the control unit 131 monitors the feedback signal $g(\tau_1)$ and causes the irradiating unit 110 to shape the wavefront of the irradiation light 151 so that the feedback signal $g(\tau_1)$ does not increase or attenuate. In other words, the wavefront is optimized in step S10 so that the detecting unit 120 can detect the propagation light that has avoided a dynamically changing region that affects the correlation function (such as the vascular area in the second area) as fully as possible. In other words, the wavefront is optimized so that the exit light that mainly propagates through the non-vascular area of the first area is measured.

Next, in step S20, the control unit 131 causes the irradiating unit 110 to irradiate the target 190 with the irradiation light 151 having the wavefront shaped in step S10 and measures as a measurement signal a light intensity $V_1$ (first measurement signal) different from the feedback signal $g(\tau_1)$ using the detector 121.

Next, in step S30, similarly to step S20, the control unit 131 monitors the feedback signal $g(\tau_1)$ and executes the WFS. More specifically, the control unit 131 acquires the feedback signal in step S31, and shapes the wavefront of the irradiation light 151 so that the feedback signal becomes smaller in step S32. That is, in step S30, the control unit 131 performs the WFS so that the feedback signal $g(\tau_1)$ becomes smaller (attenuates). Therefore, the wavefront is optimized so that the detecting unit 120 detects propagation light that has been affected by the dynamic scattering changes due to blood flow or the like. In other words, the WFS is executed using the vascular area of the second area to be measured.

Next, in step S40, the control unit 131 causes the irradiating unit 110 to irradiate the target 190 with the irradiation light 151 having the wavefront shaped in step S30 and measures the light intensity $V_2$ (second measurement signal) as the measurement signal. In the measurement of step S40, the control unit 131 may execute the WFS of step S30 as needed to update the wavefront of the irradiation light 151 as needed, and execute the measurement of step S40.

Next, in step S50, the control unit 131 compares and evaluates the two measurement signals obtained in steps S20 and S40. As described in the first embodiment, the ratio or difference between the light intensities $V_1$ and $V_2$ may be evaluated. Alternatively, the measurement result may be analyzed based on a model such as a transport equation and a diffusion equation, and the result may be evaluated. For example, in a case where an absorption wavelength of a specific target such as blood hemoglobin is measured with the irradiation light 151, the absorbance or the relative concentration of the target may be evaluated based on the measurement signal.

Similarly to the first embodiment, this embodiment can perform pre-measurement before step S10 to determine a parameter such as a measurement condition in advance. In this embodiment, the detection position (distance ρ) illustrated in FIG. 2 may be fixed or variable. In the latter case, the detection positions measured in steps S10 and S20 and steps S30 and S40 may be changed based on the results of pre-measurement.

As a variation of this example, the autofluorescence of the target 190 may be used. A wavelength range of 300 to 400 nm is used for the light source 101. For example, in steps S10 and S30 of FIG. 3, the detector 121 receives light having a wavelength that is excited by the irradiation light 151 and emitted by autofluorescence as a WFS feedback signal. The wavefront shaping unit 111 can shape the wavefront of the irradiation light 151 so that the fluorescence intensity received by the detector 121 increases. In the subsequent measurements in steps S20 and S40, the correlation function may be evaluated by measuring variations with time in the light intensity of autofluorescence based on the DLS. Here, in steps S10 and S30, the detecting unit 120 may have an excitation light cut filter such that only fluorescence is measured by the detector 121. Depending on the type of autofluorescence, the depth of the light source inside the target 190 can be estimated. For example, advanced glycation end products, NADH, and the like may be used as autofluorescence. The light source 101 may be a light source having a plurality of wavelengths in order to handle a plurality of phosphors and various measurement items.

In the measurements of steps S20 and S40, the detector 121 may receive the light emitted at the wavelength of the excitation light, the variations with time may be measured based on the DLS, and the correlation function may be evaluated.

Alternatively, the feedback signal for the WFS is not limited to the above autofluorescence, and a fluorescent contrast agent may be administered and its luminescence may be used. Steps S20 and S40 may directly measure the feedback signal as the second signal, and the light from the light source can be concentrated and irradiated onto a light emitting area inside the target 190. The effect of this concentrative irradiation may be used to treat lesions inside the target 190. In this case, a laser may be used as the light source.

The measuring apparatus according to each embodiment may not have the reflection type configuration as illustrated in FIG. 1 and may have a transmission type configuration. Various combinations of the feedback signal (first signal) for executing the WFS and the measurement signal (second signal) for acquiring target information (physiological information on a living body) are conceivable and are not limited to the above embodiments. In each embodiment, as the WFS effects, the improvement of the S/N ratio obtained as a result of scattering suppression and light concentration effect to a more localized area in the scattering medium are used to measure a living body. At this time, since the feedback signal used for the WFS is operated and controlled on the measuring apparatus side, each embodiment acquires biometric information by measuring another measurement signal that the WFS effect reaches without directly using the above feedback signal.

As described above, the measuring apparatus 100 according to each embodiment is a measuring apparatus configured to acquire information on a target, and includes an irradiating unit 110, a detecting unit 120, and a processing unit 130. The processing unit 130 causes the irradiating unit 110 to shape the wavefront of the irradiation light by feeding back the first signal (feedback signal) output from the detecting unit 120 that has received the exit light. The processing unit 130 acquires information about the specific area using the second signal (measurement signal) output from the detecting unit 120 that has received the exit light from the target by irradiating the target with the irradiation light having the shaped wavefront.

The first signal or the second signal may be a light intensity measured based on a distance between the irradiating position where the irradiating unit 110 irradiates the target with the irradiation light and the detection position where the detecting unit 120 detects the exit light. Alternatively, the first signal or second signal may be a signal based on a correlation function calculated by dynamic light scattering (DLS), or a fluorescence intensity emitted by autofluorescence (or fluorescent dye). The processing unit 130 may monitor changes in the information on the target by comparing the second signal measured for a first area and the second signal measured for a second area that are at least two different specific areas.

The irradiating unit 110 may shape the wavefront of the irradiation light so as to reduce the first signal obtained for the first area, and shapes the wavefront of the irradiation light so as to increase the first signal obtained for the second area. The target information may be physiological information inside a living body, the first area may be a non-vascular area in the living body, and the second area may be a vascular area in the living body. The processing unit 130 may use the second signal for the non-vascular area as reference data, and monitors a change in the second signal for the vascular area relative to the reference data.

Other Embodiments

Embodiment(s) of the disclosure can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read-only memory (ROM), a storage of distributed computing systems, an optical disc (such as a compact disc (CD), digital versatile disc (DVD), or Blu-ray Disc (BD)™), a flash memory device, a memory card, and the like.

Each embodiment can measure a more local physiological parameter in a living body with an excellent S/N ratio by suppressing scattering and limiting a measurement area in the living body as a target. Therefore, each embodiment can provide a measuring apparatus, a measuring method, and a storage medium, each of which can measure target information with high accuracy using light.

While the disclosure has been described with reference to embodiments, it is to be understood that the disclosure is not limited to the disclosed embodiments. The scope of the following claims is to be accorded the broadest interpretation so as to encompass all such modifications and equivalent structures and functions.

For example, each embodiment has described a measuring apparatus and a measuring method configured to acquire physiological information in a living body as information on a target, but the disclosure is not limited to this example, and can be applied to other target measurements.

What is claimed is:

1. A measuring apparatus configured to acquire information on a target, the measuring apparatus comprising:

an irradiating unit configured to irradiate a specific area of the target with irradiation light;

a detecting unit configured to receive exit light from the target which is caused by irradiating the specific area with the irradiation light; and a processing unit configured to process a signal output from the detecting unit, wherein the processing unit causes the irradiating unit to shape a wavefront of the irradiation light by feeding back a first signal output from the detecting unit that has received the exit light, and wherein the processing unit acquires information about the specific area using a second signal output from the detecting unit that has received exit light from the target which is caused by irradiating the specific area with irradiation light having the shaped wavefront, wherein the processing unit monitors changes in the information on the target by comparing the second signal measured for a first area and the second signal measured for a second area, and the first area and the second area are two different specific areas, and wherein the processing unit uses the second signal for the first area as reference data, and monitors a change in the second signal for the second area relative to the reference data.

2. The measuring apparatus according to claim 1, wherein the first signal or the second signal is a light intensity measured based on a distance between an irradiating position where the irradiating unit irradiates the target with the irradiation light and a detection position where the detecting unit detects the exit light, a signal based on a correlation function calculated by dynamic light scattering, or a fluorescence intensity emitted by fluorescent dye.

3. The measuring apparatus according to claim 1, wherein the irradiating unit shapes the wavefront of the irradiation light so as to maximize or minimize the first signal.

4. The measuring apparatus according to claim 1, wherein the irradiating unit includes a spatial light modulator, and shapes the wavefront of the irradiation light through phase modulation or amplitude modulation using the spatial light modulator based on a base pattern.

5. The measuring apparatus according to claim 1, wherein the irradiating unit shapes the wavefront of the irradiation light so as to reduce the first signal obtained for the first area, and wherein the irradiating unit shapes the wavefront of the irradiation light so as to increase the first signal obtained for the second area.

6. The measuring apparatus according to claim 1, wherein the information on the target is physiological information inside a living body, wherein the first area is a non-vascular area in the living body, and wherein the second area is a vascular area in the living body.

7. The measuring apparatus according claim 1, wherein the detecting unit includes a first detector and a second detector, wherein the first detector receives the exit light that has propagated through the first area as the specific area and exited from the target, and wherein the second detector receives the exit light that has propagated through the second area as the specific area and exited from the target.

8. The measuring apparatus according to claim 1, wherein the processing unit causes the irradiating unit to shape the wavefront of the irradiation light by feeding back the first signal from the detecting unit that has received the exit light that has propagated through the first area as the specific area and exited from the target,
   wherein the processing unit measures the second signal by causing the irradiating unit to irradiate the target with first irradiation light that has the shaped wavefront,
   wherein the processing unit causes the irradiating unit to shape the wavefront of the irradiation light by feeding back the first signal obtained from the detecting unit that has received exit light that has propagated through the second area as the specific area and exited from the target,
   wherein the processing unit measures the second signal by causing the irradiating unit to irradiate the target with second irradiation light that has the shaped wavefront, and
   wherein the processing unit acquires the information on the target by comparing the second signal based on the first irradiation light and the second signal based on the second irradiation light.

9. A measuring apparatus configured to acquire information on a target, the measuring apparatus comprising:
   an irradiating unit configured to irradiate a specific area of the target with irradiation light;
   a detecting unit configured to receive exit light from the target which is caused by irradiating the specific area with the irradiation light; and
   a processing unit configured to process a signal output from the detecting unit,
   wherein the processing unit causes the irradiating unit to shape a wavefront of the irradiation light by feeding back a first signal output from the detecting unit that has received the exit light,
   wherein the processing unit acquires information about the specific area using a second signal output from the detecting unit that has received exit light from the target which is caused by irradiating the specific area with irradiation light having the shaped wavefront, and
   wherein the processing unit measures the second signal based on a parameter relating to decay or delay time of a correlation function.

10. A measuring method configured to acquire information on a target, the measuring method comprising:
   irradiating a specific area of the target with irradiation light;
   receiving first exit light from the target, which is caused by irradiating the specific area with the irradiation light, and outputting a first signal based on the received first exit light;
   shaping a wavefront of the irradiation light by feeding back the first signal; and
   receiving second exit light from the target, which is caused by irradiating the specific area with the irradiation light having the shaped wavefront, outputting a second signal based on the received second exit light, and acquiring information about the specific area using the second signal,
   wherein changes in the information on the target are monitored by comparing the second signal measured for a first area and the second signal measured for a second area, and the first area and the second area are two different specific areas, and
   wherein the second signal for the first area is used as reference data, and a change in the second signal for the second area is monitored relative to the reference data.

11. A non-transitory computer-readable storage medium storing a program that causes a computer to execute the measuring method according to claim 10.

* * * * *